United States Patent
Solomon et al.

(10) Patent No.: US 10,071,209 B2
(45) Date of Patent: Sep. 11, 2018

(54) ENHANCED INFUSION-SITE PAIN-REDUCTION FOR DRUG-DELIVERY DEVICES

(71) Applicant: SteadyMed Ltd., Rehovot (IL)

(72) Inventors: Ian Solomon, Jerusalem (IL); Jacob Rand, Herzliya (IL); Jonathan Rigby, San Ramon, CA (US)

(73) Assignee: SteadyMed Ltd., Rehovot (IL)

( * ) Notice: Subject to any disclaimer, the term of this patent is extended or adjusted under 35 U.S.C. 154(b) by 564 days.

(21) Appl. No.: 14/384,131

(22) PCT Filed: Mar. 11, 2013

(86) PCT No.: PCT/IL2013/050223
§ 371 (c)(1),
(2) Date: Sep. 9, 2014

(87) PCT Pub. No.: WO2013/136327
PCT Pub. Date: Sep. 19, 2013

(65) Prior Publication Data
US 2015/0045718 A1    Feb. 12, 2015

Related U.S. Application Data

(60) Provisional application No. 61/670,128, filed on Jul. 11, 2012, provisional application No. 61/611,015, filed on Mar. 15, 2012.

(51) Int. Cl.
*A61N 1/30*    (2006.01)
*A61M 5/42*    (2006.01)
(Continued)

(52) U.S. Cl.
CPC ........... *A61M 5/422* (2013.01); *A61N 1/0456* (2013.01); *A61N 1/0476* (2013.01);
(Continued)

(58) Field of Classification Search
CPC . A61M 5/422; A61M 5/14248; A61N 1/0476; A61N 1/0456; A61N 1/0492; A61N 1/36021
(Continued)

(56) References Cited

U.S. PATENT DOCUMENTS 4,842,598 A    6/1989    Tran
4,843,598 A    6/1989    Medlin
(Continued)

FOREIGN PATENT DOCUMENTS

CA    2812877 A1    4/2012
DE    3621846 A1    1/1988
(Continued)

OTHER PUBLICATIONS

PCT/IL2013/050223 International Search Report, dated Jun. 24, 2013, 4 pages.
(Continued)

*Primary Examiner* — Edelmira Bosques
*Assistant Examiner* — Tiffany Legette-Thompson
(74) *Attorney, Agent, or Firm* — Kilpatrick Townsend & Stockton LLP (57) ABSTRACT

The present invention provides an infusion-patch comprising; a cannula; a base; at least one adhesive region in said base suitable for skin attachment; at least one skin-access area within said base; and at least one conduit in fluid connection with said at least one skin access area, wherein said at least one conduit in fluid connection with said at least one skin access area facilitates the transfer of an anesthetic substance within at least a first anesthetic-reservoir which may be removably attached and in fluid connection with said at least one contact area, promoting delivery of said anesthetic substance to said at least one skin-access areas, and wherein said anesthetic substance delivered to said skin-
(Continued)

access areas may be at least partially replenished without removing said infusion-patch.

20 Claims, 5 Drawing Sheets

(51) Int. Cl.
   *A61N 1/36* (2006.01)
   *A61N 1/04* (2006.01)
   *A61M 5/142* (2006.01)
(52) U.S. Cl.
   CPC ....... *A61N 1/0492* (2013.01); *A61N 1/36021* (2013.01); *A61M 5/14248* (2013.01)
(58) Field of Classification Search
   USPC .......................................... 604/20, 112, 506
   See application file for complete search history.

(56) References Cited

U.S. PATENT DOCUMENTS

| | | |
|---|---|---|
| 4,886,514 A | 12/1989 | Maget |
| 5,062,834 A | 11/1991 | Gross et al. |
| 5,102,389 A | 4/1992 | Hauser |
| 5,108,852 A | 4/1992 | Tomantschger et al. |
| 5,109,850 A | 5/1992 | Blanco et al. |
| 5,134,046 A | 7/1992 | Chow et al. |
| 5,318,557 A | 6/1994 | Gross |
| 5,354,264 A | 10/1994 | Bae et al. |
| 5,436,372 A | 7/1995 | Yoshida et al. |
| 5,438,249 A | 8/1995 | Chang et al. |
| 5,505,706 A | 4/1996 | Maus et al. |
| 5,527,288 A | 6/1996 | Gross et al. |
| 5,563,004 A | 10/1996 | Buzzelli et al. |
| 5,643,207 A | 7/1997 | Rise |
| 5,677,083 A | 10/1997 | Tomiyama |
| 5,814,020 A | 9/1998 | Gross |
| 5,827,233 A | 10/1998 | Futagawa et al. |
| 5,848,991 A | 12/1998 | Gross et al. |
| 5,938,640 A | 8/1999 | Maget et al. |
| 5,980,741 A | 11/1999 | Schnell et al. |
| 6,150,053 A | 11/2000 | Murata et al. |
| 6,186,982 B1 | 2/2001 | Gross et al. |
| 6,296,967 B1 | 10/2001 | Jacobs et al. |
| 6,312,409 B1 | 11/2001 | Gross |
| 6,322,532 B1 | 11/2001 | D'Sa et al. |
| 6,358,239 B1 | 3/2002 | Rake et al. |
| 6,377,848 B1 | 4/2002 | Garde et al. |
| 6,400,489 B1 | 6/2002 | Suzuki et al. |
| 6,465,125 B1 | 10/2002 | Takami et al. |
| 6,506,520 B1 | 1/2003 | Inoue et al. |
| 6,534,218 B1 | 3/2003 | Okada et al. |
| 6,537,249 B2 | 3/2003 | Kriesell et al. |
| 6,537,250 B1 | 3/2003 | Kriesel |
| 6,577,039 B2 | 6/2003 | Ishida et al. |
| 6,589,229 B1 | 7/2003 | Connelly et al. |
| 6,733,485 B1 | 5/2004 | Whitehurst et al. |
| 6,982,514 B1 | 1/2006 | Lu et al. |
| 7,242,134 B2 | 7/2007 | Wallace et al. |
| 7,364,568 B2 | 4/2008 | Angel et al. |
| 7,541,715 B2 | 6/2009 | Chiang et al. |
| 8,834,454 B2 | 9/2014 | Genosar et al. |
| 9,011,376 B2 | 4/2015 | Goldstein |
| 2002/0107480 A1 | 8/2002 | Kriesel et al. |
| 2002/0156461 A1 | 10/2002 | Joshi |
| 2002/0169439 A1 | 11/2002 | Flaherty |
| 2003/0014014 A1 | 1/2003 | Nitzan |
| 2003/0205582 A1 | 11/2003 | Joshi et al. |
| 2004/0059282 A1 | 3/2004 | Flock et al. |
| 2004/0068224 A1 | 4/2004 | Couvillon et al. |
| 2004/0115068 A1 | 6/2004 | Hansen et al. |
| 2004/0115523 A1 | 6/2004 | Hommura et al. |
| 2004/0115530 A1 | 6/2004 | Maeda et al. |
| 2004/0138612 A1 | 7/2004 | Shermer et al. |
| 2005/0096587 A1 | 5/2005 | Santini et al. |
| 2006/0052768 A1 | 3/2006 | Joshi et al. |
| 2006/0069344 A1 | 3/2006 | Southam et al. |
| 2006/0102455 A1 | 5/2006 | Chiang et al. |
| 2006/0106346 A1 | 5/2006 | Sullivan et al. |
| 2006/0200073 A1 | 9/2006 | Radmer et al. |
| 2008/0188779 A1 | 8/2008 | Vellero |
| 2008/0281270 A1 | 11/2008 | Cross et al. |
| 2009/0069746 A1* | 3/2009 | Miller ............... A61M 5/14244 604/67 |
| 2009/0093772 A1 | 4/2009 | Genosar et al. |
| 2009/0312706 A1* | 12/2009 | Shantha ................. A61K 9/703 604/112 |
| 2010/0022992 A1 | 1/2010 | Genosar et al. |
| 2010/0056874 A1 | 3/2010 | Dijksman et al. |
| 2010/0106088 A1* | 4/2010 | Yodfat ................. A61B 5/6849 604/112 |
| 2010/0130931 A1 | 5/2010 | Yodfat et al. |
| 2010/0152658 A1 | 6/2010 | Hanson et al. |
| 2010/0266638 A1* | 10/2010 | Turkel ............... A61K 38/4893 424/239.1 |
| 2010/0274221 A1* | 10/2010 | Sigg ........................ A61B 5/036 604/505 |
| 2011/0098652 A1 | 4/2011 | Hasted et al. |
| 2011/0160655 A1 | 6/2011 | Hanson et al. |
| 2011/0306929 A1 | 12/2011 | Levesque et al. |
| 2012/0041338 A1 | 2/2012 | Chickering, III |
| 2012/0042517 A1 | 2/2012 | Tronnes et al. |
| 2012/0238849 A1 | 9/2012 | Holtzclaw et al. |
| 2014/0148761 A1 | 5/2014 | Rotem et al. |
| 2014/0163339 A1 | 6/2014 | Goldstein et al. |
| 2014/0171867 A1 | 6/2014 | Walsh et al. |
| 2015/0017493 A1 | 1/2015 | Genosar et al. |
| 2015/0038907 A1 | 2/2015 | Rotem |
| 2016/0361491 A1 | 12/2016 | Shaked et al. |
| 2017/0304532 A1 | 10/2017 | Rotem |
| 2018/0035935 A1 | 2/2018 | Goldstein et al. |

FOREIGN PATENT DOCUMENTS

| | | |
|---|---|---|
| DE | 19809483 A1 | 9/1999 |
| EP | 0676214 A1 | 10/1995 |
| EP | 1912690 A1 | 4/2008 |
| EP | 2621558 A1 | 8/2013 |
| EP | 2825225 A1 | 1/2015 |
| EP | 2827923 A1 | 1/2015 |
| GB | 2221394 A | 2/1990 |
| IL | 169807 | 2/2006 |
| JP | 02-131376 A | 5/1990 |
| JP | 04-127885 A | 4/1992 |
| WO | 97/010012 A1 | 3/1997 |
| WO | 01/51108 A1 | 7/2001 |
| WO | 2002/069935 A1 | 9/2002 |
| WO | 2004/067066 A1 | 2/2003 |
| WO | 2004006982 A2 | 1/2004 |
| WO | 2005/124918 A2 | 12/2005 |
| WO | 2007/010522 A1 | 1/2007 |
| WO | 2007/129317 A1 | 11/2007 |
| WO | 2008/062335 A1 | 5/2008 |
| WO | 2008/122983 A1 | 10/2008 |
| WO | 2001/021234 A1 | 3/2009 |
| WO | 2011/075100 A1 | 6/2011 |
| WO | 2012/042517 A1 | 4/2012 |
| WO | 2013/136327 A1 | 9/2013 |
| WO | 2013/140395 A1 | 9/2013 |

OTHER PUBLICATIONS

Lee et al., "Battery Dimensional Changes Occuring During Charge/Discharge Cycles—Thin Rectangular Lithium Ion and Polymer Cells," Journal of Power Sources, 119-121: 833-837 (2003).
European Search Report dated Apr. 13, 2016 for European Patent Application 15171662.8, all pages.
International Search Report and Written Opinion for PCT/IL2007/000548 dated Sep. 18, 2007, all pages.
International Search Report and Written Opinion for PCT/IL2006/000769 dated Oct. 30, 2006, all pages.

(56) References Cited

OTHER PUBLICATIONS

International Preliminary Report on Patentability for PCT/IL2006/000769 dated Jan. 22, 2008, all pages.
International Preliminary Report on Patentability for PCT/IL2013/050223 dated Sep. 16, 2014, all pages.
International Search Report and Written Opinion for PCT/IL2013/050240 dated Jul. 2, 2013, all pages.
International Preliminary Report on Patentability for PCT/IL2013/050240 dated Sep. 23, 2014, all pages.
International Preliminary Report on Patentability for PCT/IL2007/000548 dated Nov. 11, 2008, all pages.
International Search Report and Written Opinion for PCT/IL2011/000757 dated Jan. 11, 2012, all pages.
International Preliminary Report on Patentability for PCT/IL2011/000757 dated Apr. 2, 2013, all pages.
Notice of opposition to a European patent for Patent No. EP 2015806 Jun. 1, 2010, 16 pages.
European Search report dated Mar. 4, 2016 in European Patent Application 11732228.8, all pages.

\* cited by examiner

Figure 4b

ENHANCED INFUSION-SITE PAIN-REDUCTION FOR DRUG-DELIVERY DEVICES

RELATED APPLICATIONS

This application is a 35 USC § 371 U.S. National Stage Entry of PCT Application Serial No. PCT/IL2013/050223 (WO 2013/136327) filed on Mar. 11, 2013, which claims priority to U.S. Provisional Application No. 61/611,015, filed on Mar. 15, 2012, and U.S. Provisional Application No. 61/670,128, filed on Jul. 11, 2012, which are each incorporated herein in the entirety by reference.

FIELD OF THE INVENTION

The present invention is in the field of liquid drug-delivery, in relation to infusible or injectable liquid drug delivered subcutaneously. In particular, the present invention provides a device and method for addressing the problem of pain associated with certain drug-delivery and describes a system for minimizing such pain integrated within the base of a patch such as an infusion set or a patch-pump and a method of use thereof.

BACKGROUND TO THE INVENTION

The pain associated with the insertion of needles or cannulas into the subcutaneous space is well known and can be addressed in a limited fashion by rubbing anesthetic cream into the insertion site prior to introduction of the rigid cannula (needle) or flexible cannula. Additionally, some drugs incite a stinging sensation, inflammatory response, vaso-dilatory response or pain response during injection for at least some of the duration of the injection or infusion.

Examples of drugs whose infusion causes pain at the infusion-site are adalimumab (Abbott Laboratories, Ill., USA) and treprostinil (United Therapeutics Corp., Md., USA). There are three main methods known in the art for reducing pain at the infusion-site during an injection or infusion:
(1) Preparation of the skin directly prior to the injection, whether by using an anesthetic cream, patch or topical spray containing lidocaine, for example LidoCream 4 (Golden Touch LLC, Ky., USA). The last named is a cream which is typically rubbed into the skin before application of the infusion set.
(2) Preparation of the infusion site well in advance of the injection, in order to prepare and numb the area. For example, the use of capsaicin-based patches, such as the Qutenza patch (NeurogesX, Inc., CA, USA) has been shown to have a long term effect which increases towards an optimal level over a couple of weeks.
(3) Release of an anesthetic such as lidocaine or bupivacaine from the adhesive layer of an infusion set or patch-pump, as described in US patent application #20110313391.
In approaches (1) and (3), the release of the anesthetic is typically only effective for a few hours, after which time the effect gradually drops off. Thus, when infusing a pain-causing drug for periods significantly longer that this, there is a lack of suitable systems to ensure the continuity or refreshing of the pain-relieving effect.

OBJECT OF THE INVENTION

Thus the objective of the present invention is to a means for an infusion-set or patch-pump having a renewed and/or maintaining an ongoing high-level of pain-reduction treatment of the skin-area being treated, significantly beyond what is currently achievable using the existing approaches.

It is a further object of the invention to enable the patient to determine the onset and or renewal of this pain-reducing effect at his own convenience.

It is yet a further objective of the invention to provide the above functionality while maintaining a compact delivery system, for example, without significantly increasing the size or height of the infusion-set or patch-pump.

SUMMARY OF THE INVENTION

The present invention provides a system for filling and replenishing skin-contact areas underneath an infusion-set or patch-pump (hereafter collectively termed an "infusion patch") with a pain-reducing substance, while the patient continues to have said infusion patch adhered to his skin.

Said system provides for an anesthetic or other pain-reducing drug to be delivered from a reservoir to said skin-contact areas, without disturbing the ongoing delivery of the drug from the cannula to the subcutaneous layer.

In some embodiments, this invention provides an infusion-patch comprising:
 a cannula
 a base;
 at least one adhesive region in said base suitable for skin attachment;
 at least one skin-access area within said base; and
 at least one conduit in fluid connection with said at least one skin access area,
wherein said at least one conduit in fluid connection with said at least one skin access area facilitates the transfer of an anesthetic substance within at least a first anesthetic-reservoir which may be removably attached and in fluid connection with said at least one contact area, promoting delivery of said anesthetic substance to said at least one skin-access areas, and wherein said anesthetic substance delivered to said skin-access areas may be at least partially replenished without removing said infusion-patch.

In some embodiments, the term "cannula" encompasses the device commonly known in the field of medical sciences. In some embodiments, the term "cannula" is to be understood to encompass any tube-like structure that can be inserted into the body. In some embodiments, the term "cannula" refers to a rigid cannula or flexible cannula. In some embodiments a needle is used instead of a cannula. In yet another embodiment a needle array is used.

The infusion-patches of this invention comprise a base through which a cannula inserts. Such cannula may be connected to a drug reservoir, for delivery of a drug product as described herein.

The base of the infusion-patches of this invention will also comprise at least one adhesive region suitable for skin attachment. Such adhesive region may comprise strips of adhesive material which facilitate adhesion of the infusion patches of this invention to the subject being treated. In some embodiments, such adhesive regions may comprise double-sided adhesive materials. In some embodiments, such adhesive material may be any such material known in the art, which are commonly used for adherence to skin. It will be appreciated that any such adhesive material is contemplated for inclusion in the devices and uses of this invention.

In some embodiments, the base further comprises a skin access area. In some embodiments, such skin access area is a channel in the base, which channel comprises apertures located along a length of said channel, which apertures enable release of a pain reducing substance, such as an anesthetic substance for example, contained in a liquid, cream, etc. so that such anesthetic substance delivered to said channel may be released externally from the base, so that it is in contact with the skin area to which such base is applied.

Said pain-reducing substance may, in some embodiments, comprise a local anesthetic, analgesic or anti-inflammatory compound and its contact with the skin following release from said channel reduces pain at the proximally located skin site, which in turn is proximally located to, or also comprises a site of infusion of a second substance delivered thereto.

The term "anesthetic substance", in some embodiments, refers to the use of any compound, such as a drug or biomaterial, such as a protein or peptide, which serve to reduce local infusion-site pain.

In some embodiments, such anesthetic substances may include benzocaine, butamben, dibucaine, lidocaine, oxybuprocaine, pramoxine, proparacaine, proxymetacaine, tetracaine and others. In some embodiments, such anesthetic substances may include a neurotoxin, for example a toxin isolated from *Clostridium botulinum*.

In some embodiments, the anesthetic-reservoir can either be detachable from said infusion-patch one, or integrated within the device.

In some embodiments, the infusion-patch further comprises a connector in fluid connection with said cannula, wherein said at least a first anesthetic-reservoir is external to said infusion-patch; and may be attached to said connector via a mechanism that may be removed and optionally replaced with at least a second anesthetic-reservoir.

In some aspects, when the anesthetic reservoir is detachable from the infusion-patches of this invention, such reservoir may be any convenient shape or size. In some embodiments, for example, such anesthetic-reservoir is in the form of a tube containing the anesthetic, analgesic, or anti-inflammatory substance and said tube is connected to said infusion patch via a connector attached to said infusion-patch.

According to this aspect, and in some embodiments, such connector may provide a seal so that delivery of said anesthetic, analgesic, or anti-inflammatory substance from said reservoir to said conduit diminishes or prevents escape of said substance during transfer. In some embodiments, such connector may operate via screw cap or other releasable connection which permits an appropriate seal during delivery of the substance.

According to this aspect, and in some embodiments, such connector may create a liquid connection to the skin-contact areas under said infusion-patch.

In some aspects, when the anesthetic reservoir is integrated within the device, in some embodiments, the reservoir or reservoirs containing an anesthetic, analgesic, or anti-inflammatory substance may be implemented as nodules which come into fluid connection with said skin-contact areas on rupturing of a barrier (such as a weak-weld) between said nodule and said skin-contact areas. In some embodiments, the integrated reservoir containing an anesthetic, analgesic, or anti-inflammatory substance is integrated with an actuator, which drives the patch-pump, such that said actuator drives both the drug delivery and the topical anesthetic delivery simultaneously.

In some embodiments, an infusion set according to the present invention may further comprise a series of transcutaneous electrical nerve stimulation (TENS) electrodes integrated within the skin adhesion side of said set; whereby TENS is used as a further pain-reducing element of the invention.

In some embodiments, the invention provides methods of use of the devices of this invention, providing a means of pain reduction at a site of drug delivery for any drug delivery for which such application would be beneficial.

In some embodiments, the invention provides a method of treating pulmonary arterial hypertension using the infusion-patch as herein described to deliver Treprostinil. In some embodiments, the invention provides for the use of an infusion-patch as herein described to deliver Treprostinil, for treating pulmonary arterial hypertension.

In some embodiments, the anesthetic, analgesic or anti-inflammatory for use according to this aspect, may comprise a neurotoxin, which in some embodiments, is isolated from *Clostridium botulinum*.

DETAILED DESCRIPTION OF THE FIGURES

Figure 1A:
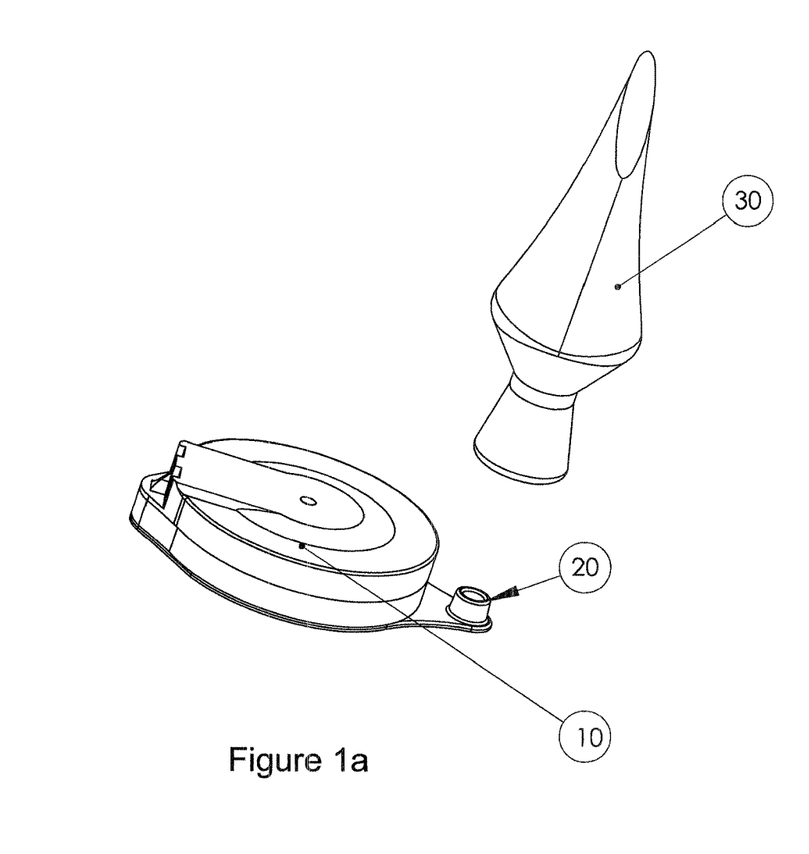
FIGS. 1a and 1b provide isometric views of a preferred embodiment of the infusion-patch of the current invention before and after connection of an anesthetic-reservoir, respectively.

A preferred embodiment of the infusion-patch of the current invention is shown in FIG. 1a, showing the infusion-patch 10 and a connector 20 for attaching an anesthetic-reservoir 30. Said infusion-patch may be either an infusion-set or a patch-pump; the difference being that a patch-pump contains the drug to be delivered integrally within it, whereas an infusion set is connected via a tube to an external infusion pump which contains the drug. In both cases, the underside (not shown) of the infusion-patch contains a subcutaneous cannula which serves to deliver the drug into the subcutaneous fat layer under the dermis. The tube shown is a preferred embodiment of an external anesthetic reservoir 30. Said tube type reservoir is convenient for storing creams and lotions, and, advantageously, typically has a thread and screw-cap type closure arrangement, which is convenient for effecting a threaded connection to the connector 20 on the infusion-patch.

Figure 1B:
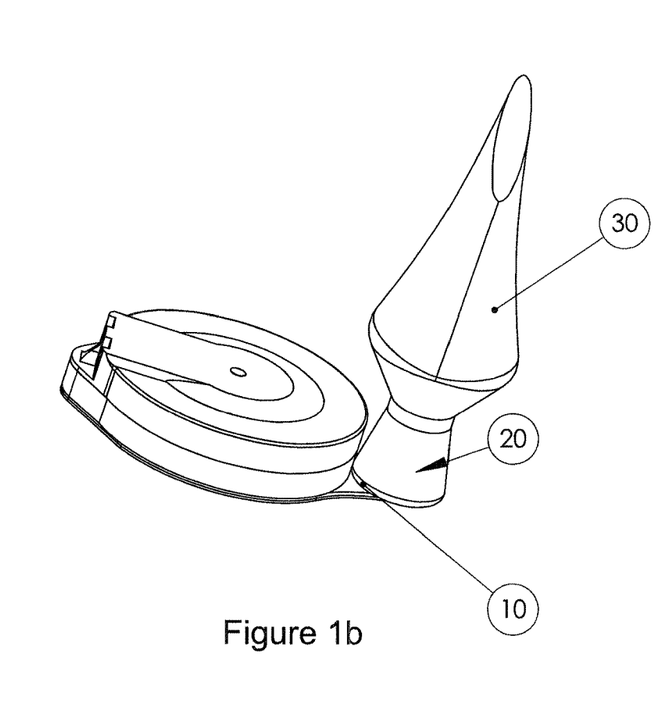

Referring now to FIG. 1b, the tube 30 which constitutes the anesthetic-reservoir in this embodiment, is shown connected to the infusion-patch 10; either by a threaded connection or by other means known in the art. Clearly any external reservoir could be used for this purpose, but, advantageously, the use of a tube provides for easy delivery of the anesthetic merely by squeezing said tube. Substances suitable for storing and using from said anesthetic-reservoir include any anesthetic, analgesic and/or anti-inflammatory drugs, including but not limited to, lidocaine or bupivacaine, salicylates, diclofenac, capsaicin, topical NSAIDs, antihistamines such as Mepyramine, topical steroids such as hydrocortisone, antipruritic agents and topical vasoconstrictive agents; either individually or in combination. Suitable formulations for such drugs or drug combinations include creams, foams and gels; for example Pluronic Lecithin Organogel (PLO Gel) which is commonly used for diclofenac administration.

Figure 2:
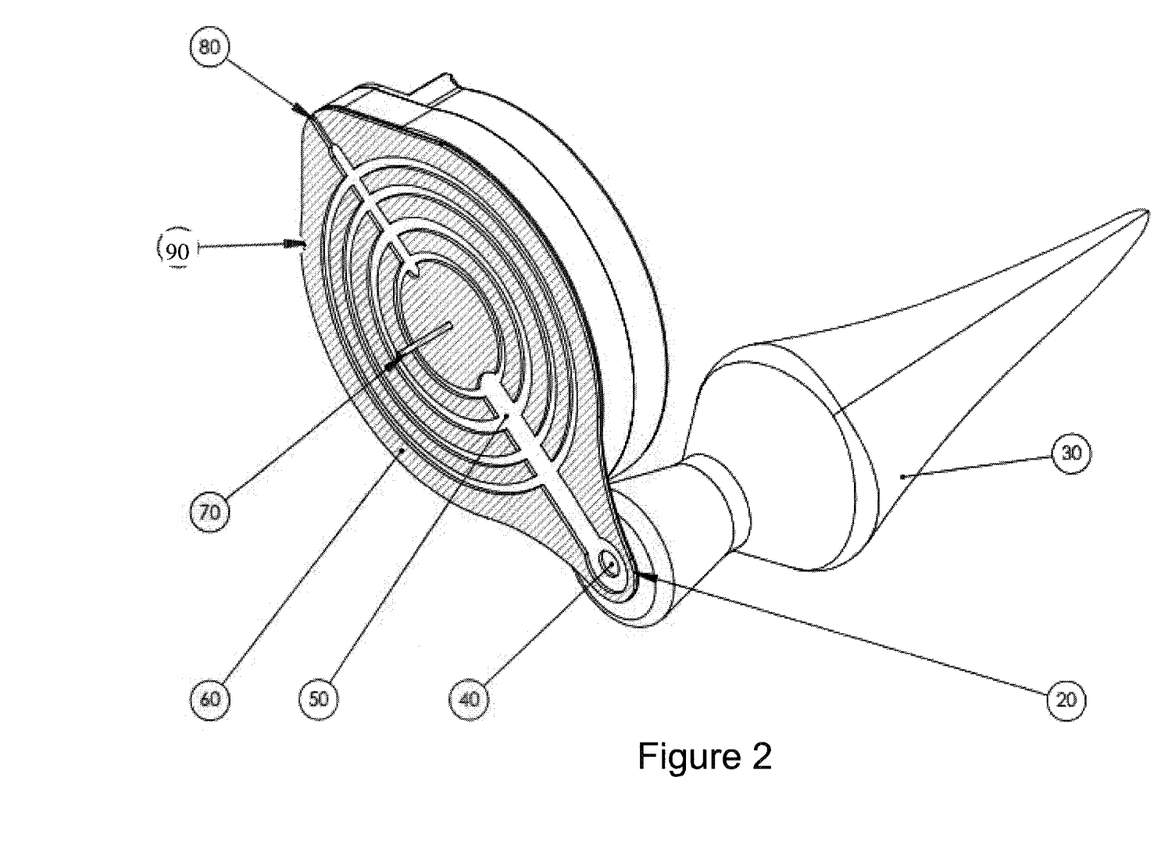
FIG. 2 provides an isometric view of said infusion-patch, showing a preferred embodiment of the structure of the skin-contact side of said patch.

Referring now to FIG. 2, the situation in which an external anesthetic-reservoir 30 (shown in this embodiment as a tube) is attached to the connector 20 is shown. In this configuration, there is a fluid connection established along a conduit 40 leading from the connector 20 to the skin-access areas 50 of the base 90 of the infusion-patch 10. Also shown in the base 90 are the adhesive areas 60 which serve to adhere the infusion-patch 10 to the skin and the cannula 70. There are a number of adhesives which typically serve this purpose, including those from 3M (MN, USA). In the preferred embodiment shown, the skin-access areas 50 have a channel structure such that they can lead the anesthetic along said skin-access areas such that said substance or excess thereof is eventually expelled from the base at one or more exit points 80.

The cannula 70 may be either a rigid or a flexible one, as it known in the art; the key point being that it serves to deliver a drug to the subcutaneous fat layer underneath the dermis.

Figure 3:
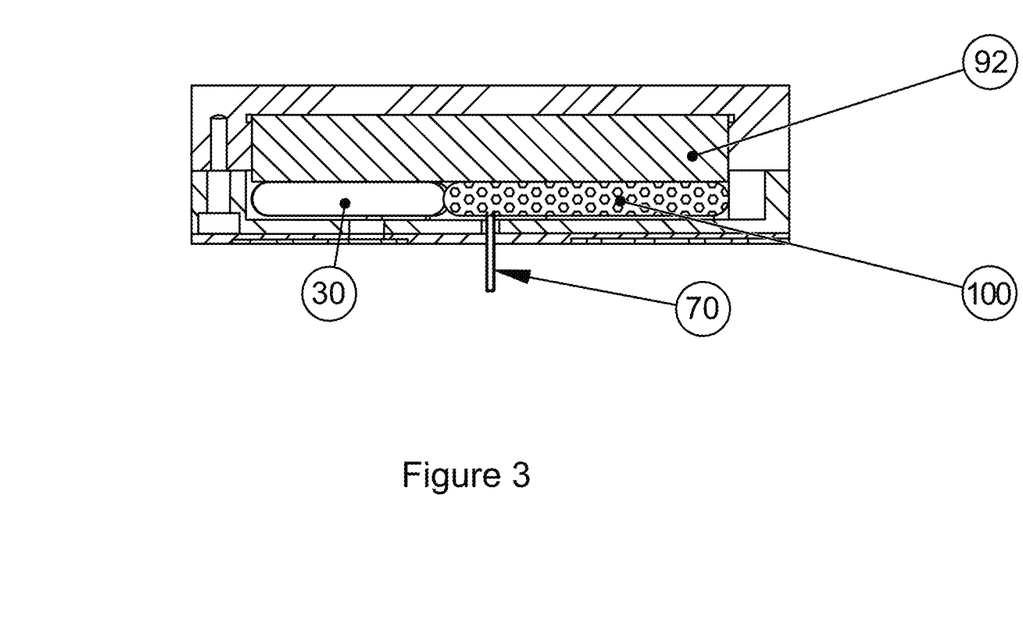
FIG. 3 provides a cross-sectional view of a further preferred embodiment of said infusion-patch, where the anesthetic-reservoir is integrated into the infusion-patch.

Referring now to FIG. 3, the case where the infusion-patch is a patch-pump is shown. In this preferred embodiment, an actuator 92 expands against an integral flexible drug-reservoir 100 containing the drug to be delivered. In use, the drug-reservoir 100 is in fluid connection with the cannula, such that the compression of said drug-reservoir causes the drug to be delivered. In the embodiment shown, said actuator 92 also compresses the anesthetic-reservoir 30 which is in fluid connection via the conduit (not shown) to the skin-access areas 50 in the base 90 of the pump.

Figure 4A:
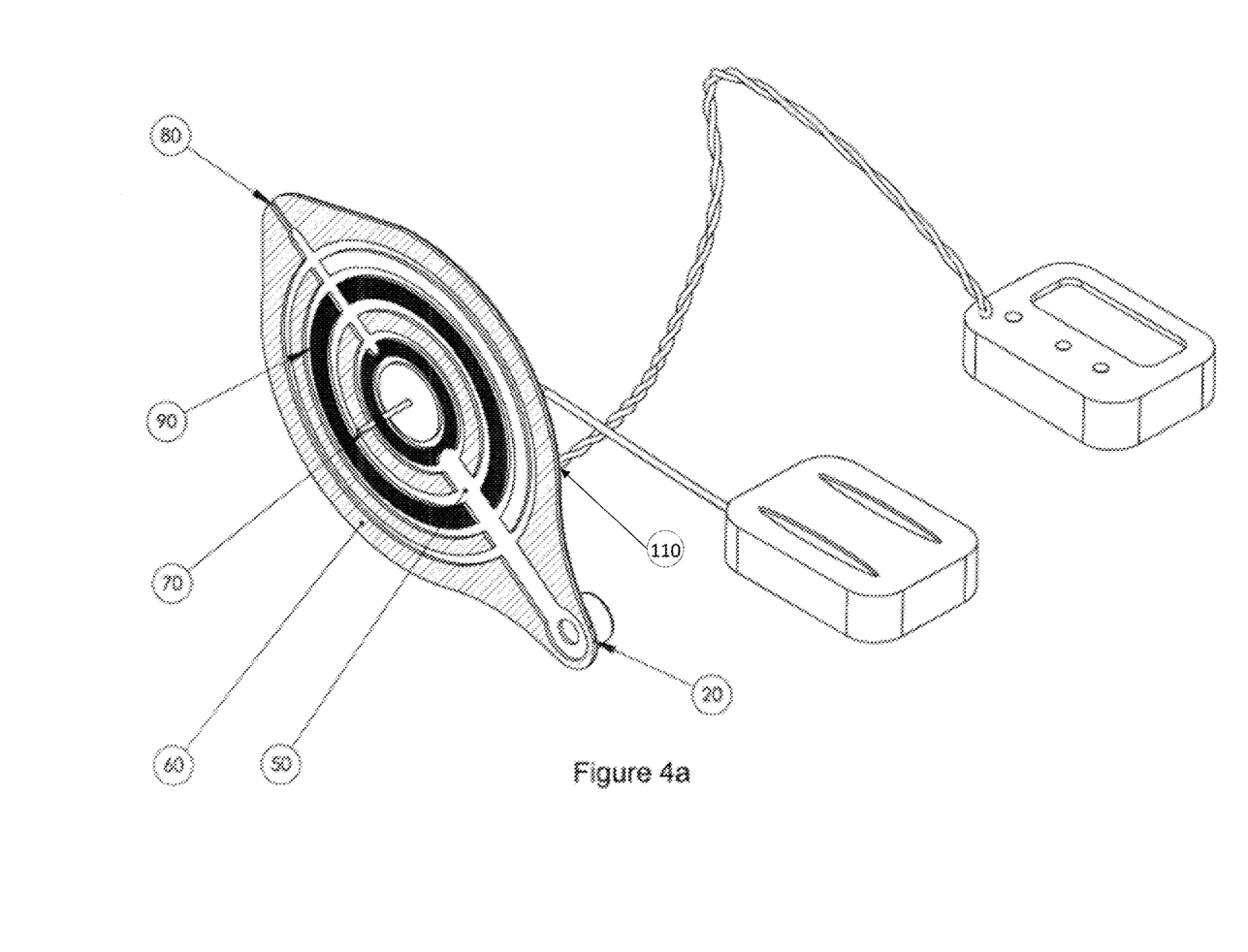
FIG. 4a provides an isometric view of a preferred embodiment of an enhanced infusion set integrating TENS electrodes in its underside.
Figure 4B:
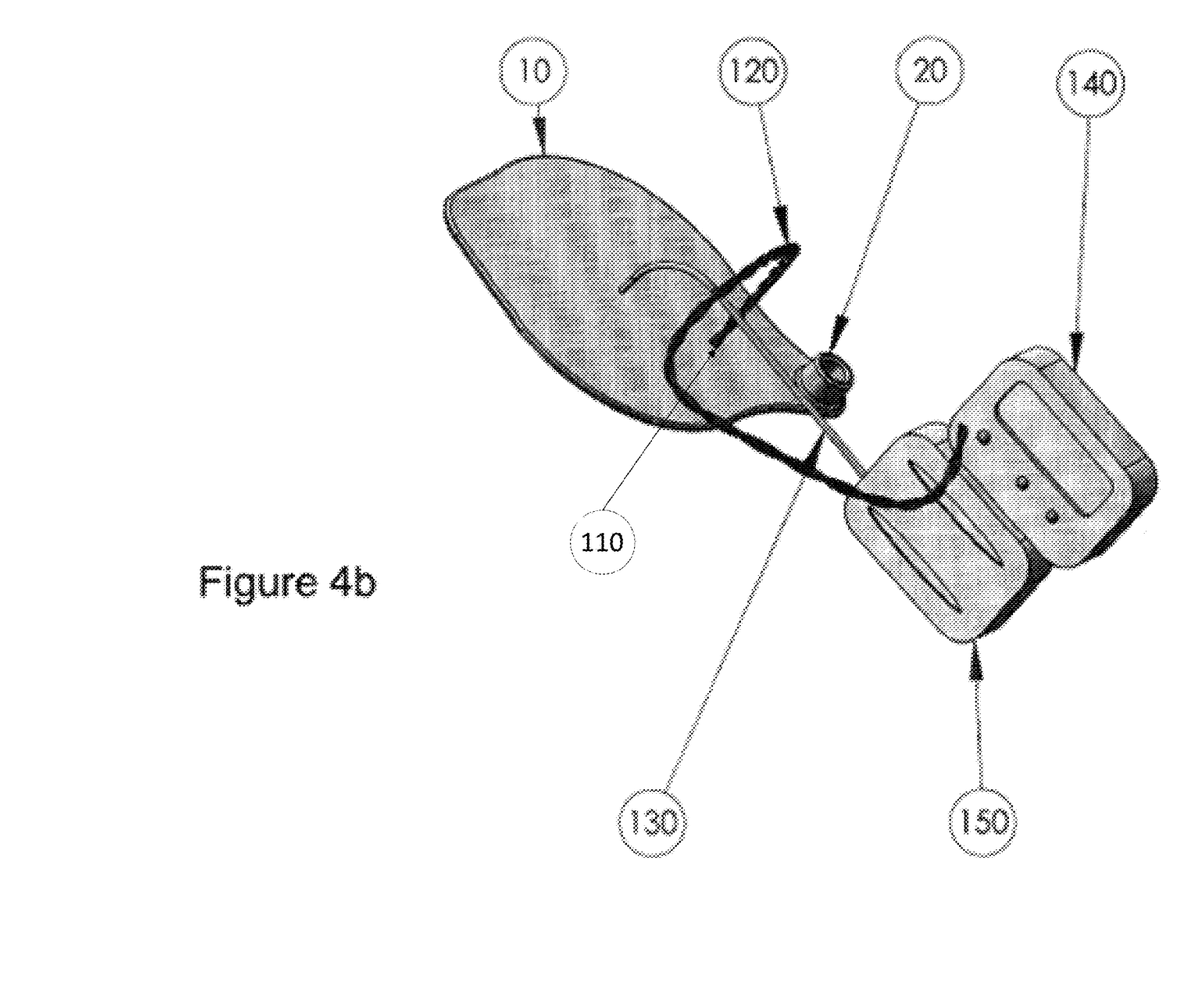
FIG. 4b provides an isometric view of the set of FIG. 4a, showing the connection of said set to an infusion set and TENS device.

Referring now to FIG. 4a, a preferred embodiment of an infusion set according to the present invention is shown. Looking at the base 90 of said infusion set, in addition to the skin-access areas 50 and the adhesive areas 60, a plurality of electrodes 110 are also provided in order to enable the use of TENS technology in order to further reduce the site pain. As shown in FIG. 4b, said electrodes 110 are connected by leads 120 to a TENS device 150, said device serving to Apply transcutaneous electrical nerve stimulation (TENS) to the skin area beneath the set; i.e. to use electric current to stimulate the nerves for therapeutic purposes. Also shown in FIG. 4b is the tube 30 leading from the infusion set to the infusion pump 140. For convenience it may be useful to bundle the TENS leads together with said tube. Additionally, even though the infusion pump 140 and TENS device 150 are shown here as separate units, an integrated pump/TENS unit would simplify the operation and is thereby included in the present invention.

As will be obvious to one skilled in the art, the present invention can be used in combination with one or more of the prior art pain-reduction techniques. For example, in addition to replenishing the drug in the skin-contact areas under the infusion-patch, the adhesive layer of said patch may also contain a pain-reducing drug. Additionally, the infusion site can be treated some days in advance using capsaicin and/or be rubbed with an anesthetic or anti-inflammatory cream directly before attaching the infusion-patch. Systemic pain-reduction and/or anti-inflammatory drugs may also be used in addition.

The invention claimed is:

1. An infusion-patch comprising:
   a cannula;
   a base;
   at least one adhesive region in said base suitable for skin attachment;
   at least one skin-access area within said base; and
   at least one conduit in fluid connection with said at least one skin-access area,
   wherein:
      said at least one conduit in fluid connection with said at least one skin-access area facilitates the transfer of an anesthetic substance within a first anesthetic-reservoir which is removably attached from the infusion-patch and in fluid connection with said at least one skin-access area,
      said at least one conduit providing fluid connection that allows transfer of said anesthetic substance from said first anesthetic-reservoir to said at least one skin-access area,
      said cannula is not in fluid communication with said at least one conduit, and
      said anesthetic substance delivered to said at least one skin-access area is at least partially replenished without removing said infusion-patch.

2. The infusion-patch of claim 1 further comprising an actuator and a drug-reservoir containing a drug to be delivered via said cannula, thereby constituting a patch-pump.

3. The infusion-patch of claim 1 where said cannula belongs to a group including rigid cannulas and flexible cannulas.

4. The infusion-patch of claim 1 where said first anesthetic-reservoir is integral to said infusion-patch and is compressed in order to propel the anesthetic substance through said at least one conduit.

5. The infusion-patch of claim 1, further comprising transcutaneous electrical nerve stimulation (TENS) electrodes for applying transcutaneous electrical nerve stimulation.

6. The infusion-patch of claim 1 where said anesthetic substance is in a form selected from the group consisting of including creams, liquids and foams.

7. The infusion-patch of claim 6, where said anesthetic substance comprises a compound selected from the group consisting of anesthetics, analgesics and anti-inflammatory substances.

8. The infusion-patch of claim 6, where said anesthetic substance is a toxin isolated from *Clostridium botulinum*.

9. The infusion-patch of claim 1 where said infusion-patch further comprises a connector in fluid connection with said cannula, wherein said first anesthetic-reservoir is external to said infusion-patch; and is attachable to said connector.

10. The infusion-patch of claim 9, further comprising:
   a second anesthetic-reservoir, wherein:
      said second anesthetic-reservoir is external to said infusion-patch,
      said second anesthetic-reservoir is attachable to said connector when first anesthetic-reservoir is detached from said connector.

11. The infusion-patch of claim 9, wherein the first anesthetic-reservoir is a tube.

12. A method of treating pulmonary arterial hypertension in a patient using the infusion-patch of claim 1 to deliver Treprostinil into a subcutaneous fat layer of the patient via said cannula of the infusion-patch and to deliver said anesthetic substance to a skin surface of the patient via said at least one skin-access area of the infusion-patch.

13. The method of claim 12, wherein said anesthetic substance is a neurotoxin.

14. The method of claim 12, wherein said anesthetic substance is a neurotoxin isolated from *Clostridium botulinum*.

15. The method of claim 12, wherein using the infusion-patch of claim 1 comprises squeezing the first anesthetic-reservoir to deliver said anesthetic substance to the skin surface.

16. The infusion-patch of claim 1, wherein:
said at least one skin-access area is a channel in the base.

17. The infusion-patch of claim 16, wherein:
the channel comprises apertures located along a length of said channel,
the apertures enable release of the anesthetic substance so that the anesthetic substance delivered to said channel is released externally from the base.

18. The infusion-patch of claim 17, wherein:
the apertures comprise an exit point, and
the exit point is configured to expel excess anesthetic substance from the base.

19. The infusion-patch of claim 18, wherein:
the exit point is configured to expel excess anesthetic substance in a direction different from a direction defined by a longitudinal axis along the cannula.

20. An infusion-patch comprising:
a cannula;
a base; and
a first anesthetic-reservoir containing an anesthetic substance,
wherein:
the base comprises an adhesive region suitable for attaching the infusion-patch to skin,
the base defines a channel,
the base defines an aperture along the length of the channel,
the first anesthetic-reservoir is in fluid communication with the channel and the aperture,
the cannula is not in fluid communication with the channel,
the aperture is a skin-access area where when the infusion-patch is attached to the skin and when anesthetic substance is disposed in skin-access area, the anesthetic substance is in contact with the skin,
the first anesthetic-reservoir is detachable from the base and replaceable by a second anesthetic-reservoir, and
the infusion-patch is configured such that anesthetic substance delivered to the channel is at least partially replenished without removing the infusion-patch from the skin.

* * * * *